United States Patent [19]
Harrison et al.

[11] Patent Number: 5,168,633
[45] Date of Patent: Dec. 8, 1992

[54] PRESSURE TRANSDUCER ELEVATION GAUGE

[76] Inventors: Samuel W. Harrison, 4003 Scenic Dr., Shreveport, La. 71119; Donald W. Fadely, 3139 Woodlawn Ave., Shreveport, La. 71104

[21] Appl. No.: 747,734

[22] Filed: Aug. 20, 1991

[51] Int. Cl.⁵ .......................................... A61B 19/00
[52] U.S. Cl. ...................................... 33/512; 33/833; 128/673
[58] Field of Search ................. 33/809, 832, 833, 511, 33/512; 128/673, 672, 674, 675, 748

[56] References Cited

U.S. PATENT DOCUMENTS

| | | | |
|---|---|---|---|
| 325,134 | 8/1885 | Wainwright | 33/511 |
| 1,001,814 | 8/1911 | Carr | 33/512 |
| 2,930,133 | 3/1960 | Thompson | 33/512 |
| 3,133,355 | 5/1964 | Gordon | 33/512 |
| 3,413,970 | 12/1968 | Rockwell | 128/674 |
| 3,435,819 | 4/1969 | Reynolds et al. | 128/674 |
| 3,439,424 | 4/1969 | Gloninger et al. | 33/832 |
| 3,495,525 | 2/1970 | Halligan et al. | 128/674 |
| 3,531,866 | 10/1970 | Lawler | 33/512 |
| 3,602,214 | 8/1971 | London et al. | 128/674 |
| 3,996,927 | 12/1976 | Frank | 128/673 |
| 4,134,212 | 1/1979 | Allen | 33/512 |
| 4,546,774 | 10/1985 | Haught | 128/673 |
| 4,669,484 | 6/1987 | Masters | 128/673 |
| 4,691,710 | 9/1987 | Dickens et al. | 33/379 |
| 4,846,173 | 7/1989 | Davidson | 33/512 |
| 4,928,398 | 5/1990 | Delfiner | 33/512 |

FOREIGN PATENT DOCUMENTS

| | | | |
|---|---|---|---|
| 2322178 | 11/1974 | Fed. Rep. of Germany | 128/674 |
| 2075683 | 11/1981 | United Kingdom | 128/674 |

*Primary Examiner*—Thomas B. Will
*Attorney, Agent, or Firm*—John M. Harrison

[57] ABSTRACT

A pressure transducer elevation gauge for determining the precise elevation of a physiologic pressure transducer in a heart catheter laboratory for determining hemodynamics, specifically relating to the heart. The pressure transducer elevation gauge is positioned adjacent to a reclined patient and an indicator is vertically adjusted on an upright rod or stand to the precise level, or mid-axiallary line of the patient's heart. The gauge indicator is then moved toward the foot of the bed, where it is used to precisely locate the physiologic pressure transducer at the mid-axiallary line.

20 Claims, 1 Drawing Sheet

1

PRESSURE TRANSDUCER ELEVATION GAUGE

BACKGROUND OF THE INVENTION

1. Field of the Invention

This invention relates to measuring devices in heart catheter laboratories and more particularly, to a pressure transducer elevation gauge which is used in heart catheterization laboratories to determine the precise vertical elevation of physiological pressure transducers to monitor hemodynamics, particularly relating to the heart. In a preferred embodiment, the pressure transducer elevation gauge is characterized by a vertical stand or support and a horizontal indicator adjustably attached to the support for precisely locating the elevation, or mid-axiallary line of the patient's heart while the patient is reclining. When the heart elevation, or heart mid-axiallary line is accurately determined by manipulation of the pressure transducer elevation gauge, the gauge is then moved to the foot of the bed and the physiologic pressure transducer is adjusted vertically on a corresponding support or stand to place the physiologic pressure transducer on the mid-axiallary line elevation of the patient's heart. The heart hemodynamics can then be monitored by operation of the physiologic pressure transducer in conventional fashion, with the assurance that the physiologic pressure transducer is operating at the precise mid-axiallary elevation of the patient's heart, to minimize error.

In the heart catheterization laboratories and intensive care units of hospitals and trauma units, physiologic pressure transducers are used to monitor the hemodynamics of the hearts of patients for various purposes. The accuracy of the data received from the physiologic pressure transducers depends upon the accuracy with which these devices are aligned with the mid-axiallary line of the patient's heart. Ideally, the physiologic pressure transducer should be located at the mid-axiallary line of the patient's heart to insure accurate measurement of the hemodynamics involved. Since critical pressure gradients may be measured by the physiologic pressure transducers, errors in elevation between each physiologic pressure transducer and the corresponding patient's heart may result in inaccurate medical conclusions and ineffective or erroneous treatment. Typically, the physiologic pressure transducer units must be mounted at the mid-axiallary level, that is, the level of the heart within the chest cavity, before the hemodynamic data is obtained. The pressure transducer elevation gauge of this invention is designed to first ascertain the mid-axiallary level of the heart of a reclining patient and then insure that the corresponding physiologic pressure transducer is located at this mid-axiallary level before the necessary hemodynamics are obtained.

2. Description of the Prior Art

Specific measurements for levelling physiologic pressure transducers in heart catheter laboratories, intensive care units and other patient care facilities in order to determine heart hemodynamics by operation of physiologic pressure transducers have been made in a variety of ways. One technique is to use a measuring stick, rod or staff and approximately determine the mid-axiallary level of the patient's heart and then locate the physiologic pressure transducer at this level near the foot of the bed. Other techniques include "guesstimating" this height by visual observation and other approximations preparatory to recording the desired hemodynamics.

Various patents are known in the art for determining the height of objects: U.S. Pat. No. 325,134 dated Aug. 25, 1885, entitled "Height Measure for Horses" to I. Wainwright; U.S. Pat. No. 2,930,133, dated Mar. 29, 1960, to J. C. Thompson, entitled "Apparatus To Aid In Determining Abnormal Positions of Spinal Vertebrae"; U.S. Pat. No. 3,133,355, dated May 19, 1964, to A. Gordon, entitled "Muscle Myotonometer"; U.S. Pat. No. 3,531,866, dated Oct. 6, 1970, to R. E. Lawler et al, entitled "Direct Reading Technique Caliper for X-Ray Machines"; U.S. Pat. No. 4,846,173, dated Jul. 11, 1989, to T. W. Davidson, entitled "Anterior Lateral Off-Axis Bite Block System for Radiation Therapy"; and U.S. Pat. No. 4,928,398, dated May 29, 1990, to Michael Delfiner, entitled "Anthropometer".

BRIEF DESCRIPTION OF THE DRAWING

The invention will be better understood by reference to the accompanying drawing, wherein.

DESCRIPTION OF THE PREFERRED EMBODIMENTS

Figure 1:
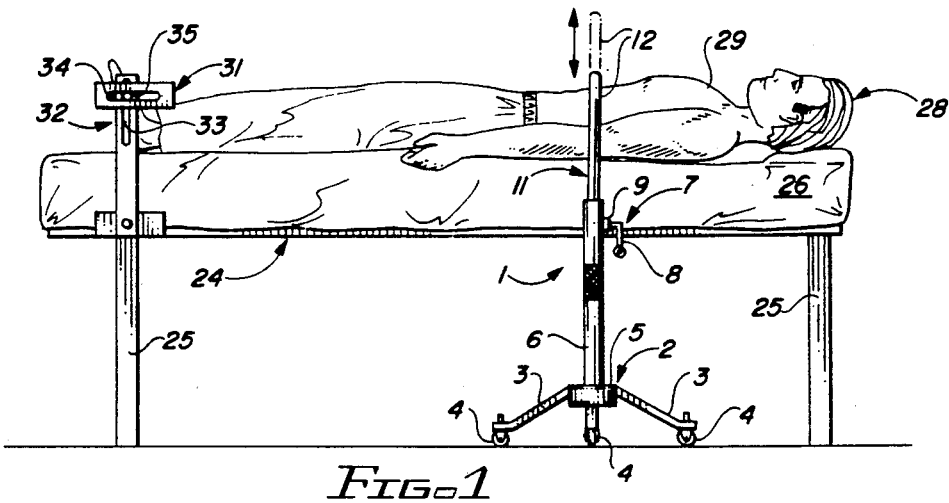
FIG. 1 is a side elevation of a preferred embodiment of the pressure transducer elevation gauge of this invention.
Figure 2:
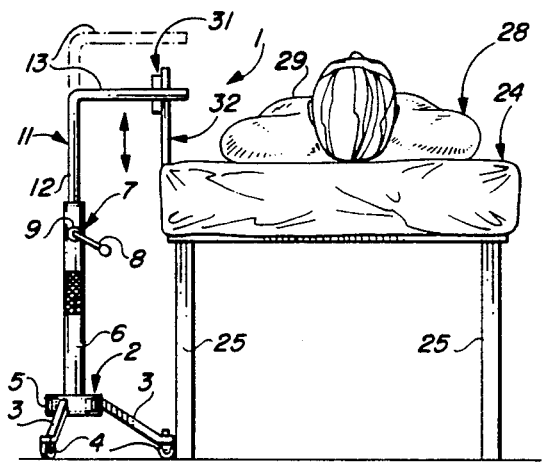
FIG. 2 is an end elevation of the pressure transducer elevation gauge illustrated in FIG. 1.

Referring initially to FIGS. 1 and 2 of the drawing, in a first preferred embodiment the pressure transducer elevation gauge of this invention is generally illustrated by reference numeral 1. The elevation gauge 1 includes a support 2, fitted with support legs 3 at the bottom thereof, having casters 4 for readily rolling the elevation gauge 1 in any direction. In a most preferred embodiment the support legs 3 of the support 2 are welded or otherwise attached to a leg base 5 which rigidly receives an upright tubular member 6. A telescoping clamp 7 is provided near the upper end of the upright tubular member 6 and is fitted with a telescoping clamp handle 8, threaded into a telescoping clamp neck 9, as illustrated. The vertical rod segment 12 of the telescoping rod 11 is telescopically mounted inside the upright tubular member 6 in concentric relationship and is secured in place at a selected elevation by manipulation of the telescoping clamp handle 8. Accordingly, it will be appreciated from a consideration of FIGS. 1 and 2 that manipulation of the telescoping clamp handle 8 in the clockwise direction tightens the extending threaded end (not illustrated) of the telescoping clamp handle 8 against the vertical rod segment 12 of the telescoping rod 11 to secure the vertical rod segment 12 at a selected elevation inside the upright tubular member 6. Manipulation of the telescoping clamp handle 8 in the counterclockwise direction therefore loosens the vertical rod segment 12 inside the upright tubular member 6 and facilitates vertical adjustment of the vertical rod segment 12 of the telescoping rod 11 with respect to the upright tubular member 6, as well as the bed 24, which receives a reclining patient 28, as illustrated. A horizontal indicator 13 projects horizontally from the vertical rod segment 12 of the telescoping rod 11 and in use, the horizontal indicator 13 is directed toward the patient 28, with the extending end of the horizontal indicator 13 located in close proximity to the chest 29 of the patient 28.

As further illustrated in FIGS. 1 and 2, the bed 24 is supported by bed legs 25 and the patient 28 is reclining on a mattress 26. A conventional pressure transducer 31 is fitted with a transducer slot 34, aligned with a transducer mount slot 33, provided in a pressure transducer mount 32 which is attached to the bed 24 for illustrative purposes. A bolt 35 extends through the transducer slot 34 and the transducer mount slot 33 and receives a wing nut (not illustrated) to adjustably secure the pressure transducer 31 on the pressure transducer mount 32.

Figure 3:
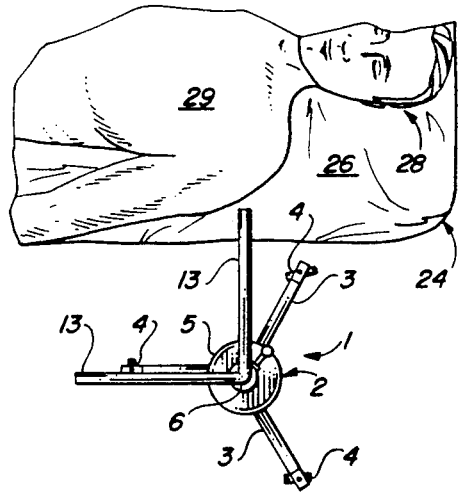
FIG. 3 is a top view, partially in section, of an alternative preferred embodiment of the pressure transducer elevation gauge illustrated in FIGS. 1 and 2.

Referring now to FIG. 3 of the drawing, in another preferred embodiment of the invention the elevation gauge 1 is characterized by a pair of horizontal indicators 13 projecting from a common vertical rod segment 12 element of the telescoping rod 11. Accordingly, as illustrated in FIG. 3, one of the horizontal indicators 13 may be directed toward the chest 29 of the patient 28, while the other horizontal indicator 13 is disposed ninety degrees from the first horizontal indicator 13 and points toward the foot of the bed at the pressure transducer 31, illustrated in FIGS. 1 and 2. This design of the horizontal indicators 13 better facilitates more accurately determining the desired mid-axiallary level of the heart in the patient 28.

Figures 4, 5:
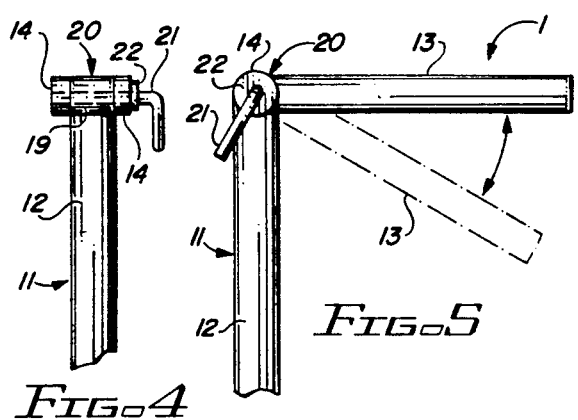
FIG. 4 is a rear elevation, partially in section, of a preferred hinge for pivoting the horizontal indicator element of the pressure transducer elevation gauge with respect to the vertical support element thereof.
FIG. 5 is a side view of the hinge illustrated i FIG. 4.

Referring now to FIGS. 4 and 5 of the drawings, in still another preferred embodiment of the invention the horizontal indicator 13 is vertically pivotable with respect to the vertical rod segment 12 of the telescoping rod 11 to facilitate easy storage of the elevation gauge 1 when not in use. In order to facilitate this pivotal relationship between the horizontal indicator 13 and the vertical rod segment 12, a cylindrical rod knuckle 19 of a rod segment hinge 20 is mounted on the extending end of the vertical rod segment 12 and the horizontal indicator 13 is fitted with a pair of cylindrical hinge plates 14, lying adjacent to and on each side of the rod knuckle 19. The threaded end (not illustrated) of a hinge locking handle 21, fitted with a flat, round locking handle collar 22, projects through aligned unthreaded openings (not illustrated) located in the adjacent hinge plate 14 and the rod knuckle 19 and into an internally-threaded cavity (not illustrated) provided in the second hinge plate 14. This design facilitates tightening of the hinge locking handle 21 and locking handle collar 22 against the adjacent hinge plate 14 to secure the hinge plates 14 tightly against the rod knuckle 19 and locate the horizontal indicator 13 in a desired pivoted position with respect to the vertical rod segment 12 of the telescoping rod 11, as illustrated in phantom in FIG. 5.

Figure 6:
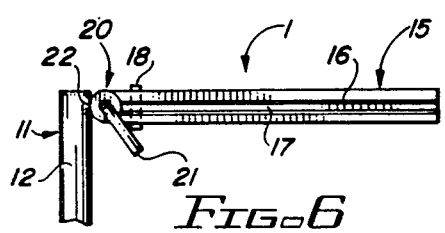
FIG. 6 is a side elevation, partially in section, of another preferred embodiment of the top segment of the pressure transducer elevation gauge of this invention.
Figure 7:
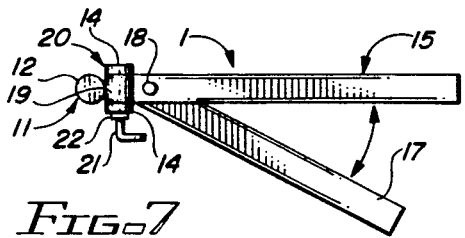
FIG. 7 is a top view of the pressure transducer elevation gauge segment illustrated in FIG. 6.

Referring now to FIGS. 6 and 7, in yet another preferred embodiment of the invention the elevation gauge 1 is characterized by a blade indicator 15 which is attached to the hinge plates 14 of the rod segment hinge 20, further secured in offset relationship to the upper end of the vertical rod segment 12 by means of the rod knuckle 19, as illustrated in FIG. 6. A hinge locking handle 21 is extended through the hinge plates 14 and rod knuckle 19 of the rod segment hinge 20, as illustrated in FIGS. 4 and 5, for the same purpose. Accordingly, it will be appreciated that the blade rod segment 15 may be pivoted from the horizontal position illustrated in FIG. 6 downwardly in the same manner as the corresponding horizontal indicator 13 in FIGS. 4 and 5. A longitudinal blade slot 16 is also provided in the blade rod segment 15 and a blade 17 is pivotally secured at one end inside the blade slot 16 by means of a blade pin 18, as further illustrated in FIGS. 6 and 7. Accordingly, it will be appreciated from a consideration of FIG. 7 that the blade 17 may be pivoted outwardly of the blade slot 16 to position the blade 17 and blade indicator 15 in the same relative position as the two horizontal indicators 13 of the telescoping rod 11 illustrated in FIG. 3.

In use, the elevation gauge 1 is initially located adjacent to the head of the bed 24 while the patient 28 reclines on his back, as illustrated in FIGS. 1 and 2. A pressure transducer 31 is provided on a pressure transducer mount 32 at the foot of the bed 24 in a conventional installation wherein vertical adjustment of the pressure transducer 31 with respect to the patient 28 and bed 24 by use of the transducer mount slot 33 and transducer slot 34, or alternative means, is easily facilitated. In the case of the elevation gauge 1 illustrated in FIGS. 1 and 2, the telescoping handle 8 of the telescoping clamp 7 is manipulated in the counterclockwise direction as viewed in FIG. 2 to loosen the vertical rod segment 12 in telescoping fashion inside the upright tubular member 6. This maneuver facilitates accurate location of the horizontal indicator 13 element of the telescoping rod 11 at the mid-axiallary line of the heart of the patient 28. When this mid-axiallary line is determined, the telescoping handle 8 ia again manipulated in a clockwise direction as viewed in FIG. 2, to lock the telescoping rod 11 in position, wherein the horizontal indicator 13 lies at the precise elevation, or mid-axiallary line, of the patient's heart. When this elevation is verified by means of the horizontal indicator 13, the elevation gauge 1 is wheeled rearwardly to the foot of the bed and the horizontal indicator 13 used to adjust the pressure transducer 31 to a corresponding level by manipulation of the bolt 35 and corresponding wing nut (not illustrated) or an appropriate alternative pin and clamp device that cooperates with the transducer mount slot 33 and transducer slot 34 illustrated in FIG. 1. This maneuver locks the pressure transducer 31 at the precise horizontal level of the horizontal indicator 13 and insures that the pressure transducer 31 is therefore at the mid-axiallary line of the heart of the patient 28. Accurate readings of the pressure transducer 31 may then be obtained with the secure knowledge that a decision which is in the best interests of the patient can be made by the doctor without pressure transducer elevation error.

Under circumstances where the elevation gauge 1 is characterized by the design illustrated in FIG. 3 when the two horizontal indicators 13 are located at the mid-axiallary line, the telescoping handle 8 is manipulated to maintain these horizontal indicators 13 at this level and one of the horizontal indicators 13 points directly toward the pressure transducer 31. Accordingly, the elevation gauge 1 can be rolled a short distance toward the foot of the bed in order to ascertain the proper height of the pressure transducer 31 by reference to the nearest horizontal indicator 13.

Referring now to FIGS. 4 and 5 of the drawing, under circumstances where the elevation gauge 1 is designed as illustrated in either FIGS. 1 and 2 or FIG. 3, after the elevation gauge 1 has been used to accurately locate a pressure transducer 31 at the mid-axiallary heart line of the patient 28, the hinge locking handle 21 of the rod segment hinge 20 is manipulated in the counterclockwise direction to facilitate folding of the horizontal indicator 13 downwardly, as illustrated in phantom in FIG. 5, for storage. Raising of the horizontal indicator 13 to the horizontal position also illustrated in FIG. 5, is facilitated by reversing this procedure and raising the horizontal indicator 13 to the horizontal position, rotating the hinge locking handle 21 in the clockwise direction and thereby locking the horizontal indicator 13 in the horizontal position. The elevation gauge 1 may then again be utilized as described above to locate the mid-axiallary line of a patient 28 illustrated in FIGS. 1 and 2.

Referring now to FIGS. 6 and 7 of the drawing, the elevation gauge 1 illustrated herein can be adjusted to the non-functional, stored configuration of the elevation gauge 1 illustrated in FIGS. 4 and 5 by manipulating the hinge locking handle 21 according to the procedure described with respect to FIGS. 4 and 5. Furthermore, the elevation gauge 1 can be adjusted to the configuration illustrated in FIG. 3 by pivoting the blade 17 outwardly of the corresponding blade slot 16 on the blade pin 18 as illustrated in FIG. 7 when it is desired to use the elevation gauge 1 illustrated in FIGS. 6 and 7. When the blade 17 is pivoted outwardly of the blade slot 16 into the 90 degree configuration of the horizontal indicators 13 illustrated in FIG. 3, the elevation gauge 1 is then utilized in the same manner as that illustrated in FIG. 3 to locate the mid-axiallary heart line of the patient 28.

It will be appreciated by those skilled in the art that the elevation gauge 1 in all of the illustrated embodiments may be optionally designed to fold or telescope at the support 2 and leg base 5 to retract the support legs 3 and orient the elevation gauge 1 into an optimum storage configuration. Furthermore, it will also be recognized that the slotted design of the pressure transducer 31 and pressure transducer mount 1 are included in the drawing for purposes of illustration only and additional transducer mounting techniques may be employed according to the knowledge of those skilled in the art.

It will be further appreciated by those skilled in the art that a determination of the mid-axiallary heart line location in a patient 28 reclining on the bed 24 involves estimation of the heart location by a doctor, nurse or technician trained in anatomy and having experience in the use of the pressure transducer 31. Accordingly, the heart location and hence, the mid-axiallary heart line or level can be determined with a high degree of accuracy to property operate the elevation gauge 1 in the manner described above.

Accordingly, while the preferred embodiments of the invention have been described above, it will be recognized and understood that various modifications may be made in the invention and the appended claims are intended to cover all such modifications which may fall within the spirit and scope of the invention.

Having described by invention with the particularity set forth above, what is claimed is:

1. A pressure transducer elevation gauge for marking the mid-axiallary line of the heart of a reclining patient, comprising base means; wheel means provided on said base means for rolling relocation of said base means; an upright member carried by said base means; rod means vertically adjustably carried by said upright member; and at least one indicating member extending from said rod means, whereby said indicating member is adjustable vertically with respect to said upright member responsive to operation of said rod means, for marking the mid-axiallary line.

2. The pressure transducer elevation gauge of claim 1 wherein said wheel means further comprises three wheels carried by said base means in spaced relationship.

3. The pressure transducer elevation gauge of claim 1 further comprising hinge means provided in said indicating member, whereby said indicating member is selectively adjustable into a horizontal position and a vertical position.

4. The pressure transducer elevation gauge of claim 3 wherein said wheel means further comprises three wheels carried by said base means in spaced relationship.

5. The pressure transducer elevation gauge of claim 1 wherein said indicating member is slidably carried by said rod means for marking the height to the mid-axiallary line.

6. The pressure transducer elevation gauge of claim 5 wherein said at least one indicating member further comprises a pair of horizontal measuring indicators disposed on said rod means in 90-degree relationship with respect to each other.

7. The pressure transducer elevation gauge of claim 6 wherein said wheel means further comprises three wheels carried by said base means in spaced relationship.

8. The pressure transducer elevation gauge of claim 5 further comprising hinge means provided in said rod means and wherein said indicating member is connected to said hinge means, whereby said indicating member is selectively adjustable into a horizontal position and a vertical position by operation of said hinge means.

9. The pressure transducer elevation gauge of claim 5 wherein said wheel means further comprises three wheels carried by said base means in spaced relationship and further comprising hinge means provided in said rod means and wherein said indicating member is connected to said hinge means, whereby said indicating member is selectively adjustable into a horizontal position and a vertical position by operation of said hinge means.

10. The pressure transducer elevation gauge of claim 1 wherein said rod means is carried by said upright member in telescoping relationship and further comprising a blade pivotally carried by said indicating member, whereby said blade is selectively pivotally extended from said indicating member in a horizontal plane.

11. The pressure transducer elevation gauge of claim 10 further comprising hinge means provided on said rod means and wherein said indicating member is connected to said hinge means, whereby said indicating member is selectively adjustable into a horizontal position and a vertical position by operation of said hinge means.

12. The pressure transducer elevation gauge of claim 10 wherein said wheel means further comprises three legs carried by said base means and three wheels carried by said legs in spaced relationship, respectively.

13. The pressure transducer elevation gauge of claim 10 wherein said wheel means further comprises three legs carried by said base means and three wheels carried by said legs in spaced relationship and further comprising a hinge provided on said rod means and wherein said indicating member is connected to said hinge, whereby said indicating member is selectively adjustable into a horizontal position and a vertical position by operation of said hinge.

14. A pressure transducer elevation gauge for marking the elevation of the mid-axiallary line of a patient's heart and gauging a pressure transducer to this mid-axiallary line, said pressure transducer elevation gauge comprising an upright member; wheel means carried by one end of said upright member for rolling said upright member from one place to another; telescoping rod means carried by said upright member; hinge means provided on said telescoping rod means; and at least one indicating member carried by said hinge means in hinged relationship, whereby said indicating member is vertically adjustable responsive to operation of said telescoping rod means and pivotally adjustable for horizontal and vertical orientation with respect to said upright member responsive to operation of said hinge means, for marking the elevation of the mid-axiallary line and gauging a pressure transducer to this mid-axiallary line.

15. The pressure transducer elevation gauge of claim 14 wherein said hinge means further comprises a knuckle carried by said telescoping rod means, a pair of hinge plates carried by said indicating member in alignment with said knuckle and a clamp handle extending through one of said hinge plates and said knuckle and threadably engaging the other one of said hinge plates, for selectively locking and releasing said indicating member in said horizontal and vertical orientation.

16. The pressure transducer elevation gauge of claim 14 wherein said at least one indicating member further comprises a pair of indicating members disposed in 90 degree relationship with respect to each other.

17. The pressure transducer elevation gauge of claim 14 wherein said indicating member further comprises a horizontal indicator projecting from said hinge means and a blade pivotally carried by said horizontal indicator, whereby said blade is selectively pivotally extended from said horizontal indicator.

18. The pressure transducer elevation gauge of claim 14 wherein said wheel means further comprises a leg base supporting said upright member and three legs carried by said leg base in spaced relationship, respectively.

19. The pressure transducer elevation gauge of claim 15 wherein said wheel means further comprises a leg base supporting said upright member and three legs carried by said leg base in spaced relationship, respectively.

20. A pressure transducer elevation gauge for marking the height of the mid-axially line of a patient's heart and gauging a pressure transducer to this mid-axiallary line, said pressure transducer elevation gauge comprising a vertical support member; wheels carried by one end of said vertical support member for rolling said support member from one place to another; a telescoping clamp carried by said support member and a telescoping clamp handle threadably engaging said telescoping clamp; a telescoping member engaging said support member and said telescoping clamp handle in vertically telescoping and adjustable relationship; a locking hinge provided on the top end of said telescoping member; and at least one indicating member carried by said locking hinge in adjustably hinged relationship, whereby said indicating member is vertically adjustable in response to operation of said telescoping member selectively pivotally adjustable for locked horizontal and vertical orientation with respect to said upright member responsive to operation of said locking hinge, for marking the elevation of the mid-axiallary line and gauging a pressure transducer to this mid-axiallary line.

* * * * *